(12) United States Patent
Brusse

(10) Patent No.: US 6,478,579 B1
(45) Date of Patent: Nov. 12, 2002

(54) ORTHODONTIC TWIN BRACKET WITH ARCHWIRE FLOOR AND SIDE WALL RELIEF

(75) Inventor: Martin Brusse, Denver, CO (US)

(73) Assignee: RMO, Inc., Denver, CO (US)

( * ) Notice: Subject to any disclaimer, the term of this patent is extended or adjusted under 35 U.S.C. 154(b) by 0 days.

(21) Appl. No.: 09/692,131

(22) Filed: Oct. 19, 2000

Related U.S. Application Data (60) Provisional application No. 60/228,575, filed on Aug. 29, 2000.

(51) Int. Cl.$^7$ .................................................. A61C 3/00
(52) U.S. Cl. ................................ 433/8; 433/10; 433/13
(58) Field of Search .................................. 433/8, 10, 13

(56) References Cited

U.S. PATENT DOCUMENTS

| | | | |
|---|---|---|---|
| 4,415,330 A | 11/1983 | Daisley et al. ................. | 433/16 |
| 4,529,382 A | 7/1985 | Creekmore ..................... | 433/9 |
| 4,531,991 A | 7/1985 | Creekmore ..................... | 433/8 |
| 4,659,309 A | 4/1987 | Merkel .......................... | 433/9 |
| 4,799,882 A | 1/1989 | Kesling ......................... | 433/8 |
| 5,044,945 A | 9/1991 | Peterson ........................ | 433/8 |
| 5,062,794 A | 11/1991 | Miura ........................... | 433/10 |
| 5,127,828 A | 7/1992 | Suyama ......................... | 433/8 |
| 5,226,814 A * | 7/1993 | Allen ............................ | 433/8 |
| 5,238,402 A * | 8/1993 | Rohlcke et al. ................. | 433/8 |
| 5,242,299 A * | 9/1993 | Yoshida ......................... | 433/8 |
| 5,299,934 A | 4/1994 | Suyama ......................... | 433/8 |
| 5,362,233 A | 11/1994 | Thompson ..................... | 433/9 |
| 5,470,228 A | 11/1995 | Franseen et al. ................ | 433/8 |
| 5,607,301 A | 3/1997 | Romas .......................... | 433/8 |
| 5,908,293 A | 6/1999 | Voudouris ..................... | 433/10 |
| 6,280,185 B1 * | 8/2001 | Palmer et al. .................. | 433/8 |

FOREIGN PATENT DOCUMENTS

| | | |
|---|---|---|
| DE | 89 03 611 | 7/1990 |
| EP | 0 317 098 A2 | 5/1989 |
| EP | 0 397 533 A2 | 11/1990 |

* cited by examiner

Primary Examiner—Cary E. O'Connor
(74) Attorney, Agent, or Firm—Sheridan Ross P.C.

(57) ABSTRACT

The present invention is directed to an orthodontic twin bracket, and in particular an orthodontic twin bracket which includes protrusions on the floor and side walls of the archwire slot in order to reduce friction. In a preferred embodiment, a bracket design is provided which incorporates one or more of the features of reduced friction, improved alignment accuracy and, ease of identification, multiple ligation options, small size and structural integrity.

9 Claims, 12 Drawing Sheets

ORTHODONTIC TWIN BRACKET WITH ARCHWIRE FLOOR AND SIDE WALL RELIEF

This application claims the benefit of Provisional application Ser. No. 60/228,575, filed Aug. 29, 2000.

FIELD OF THE INVENTION

The present invention is directed to an orthodontic twin bracket, and in particular an orthodontic twin bracket which includes protrusions on the floor and side walls of the archwire slot in order to reduce friction.

BACKGROUND OF THE INVENTION

Various methods are presently in use for correcting the orientation of irregular teeth. It is generally accepted that each tooth has a particular location in the arch and a preferred angle between its long axis and the occlusal plane. In the mouth, the tooth long axis can best be approximated by visualizing the long axis of the crown, the only visual component of the tooth. Therefore, the preferred angle referred to above can be more practically defined as the normal angle between the crown long axis of a particular tooth and the occlusal plane.

In orthodontics, an archwire is used to apply unidirectional and torquing forces to the irregular teeth. The archwire is attached to the teeth by means of a bracket assembly. Preferably, a bracket assembly is bonded directly to the facial surface of the tooth. In one embodiment of such an assembly, the tie wings are affixed to a bonding pad which is then adhered to the tooth.

Alignment of the bracket is critical. With the development of better adhesives to bond orthodontic brackets to a tooth, the sizes of the orthodontic brackets have become smaller and smaller over the years. As a consequence, and because present day adhesives have a tendency to dry rapidly, the amount of time an orthodontist has to place an orthodontic bracket on a patient's tooth, before the adhesive dries, can be reduced to a matter of seconds. Coupled with the small size of the orthodontic bracket itself, orthodontists have routinely sought new bracket designs to facilitate easy, quick and accurate alignment of orthodontic brackets on the tooth. As mentioned earlier, the occlusal plane and the tooth long axis are two reference lines which the orthodontist uses in mounting a bracket to the tooth. Orthodontists have sought bracket designs and methods which help align the archwire slot with the occlusal plane of the patient's teeth and the bracket with the tooth long axis.

Another problem encountered with small brackets is identification. Because the orthodontist typically has different brackets for different teeth, it is important and that the orthodontist be able to easily distinguish the different brackets in order to adhere the appropriate bracket to the proper tooth.

As the forces applied by the bracket and archwire move the teeth toward their correct positions, the bracket slides relative to the archwire. Therefore, it is important that the frictional forces between the archwire slot and the archwire are minimized to allow relative movement therebetween.

It is well-known that one is able to ligate an archwire to an orthodontic bracket using an elastic, elastomeric or metal ligature. In a twin edgewise orthodontic bracket, the ligature is stretched around respective undercuts of gingival and occlusal tie wings so as to overlay the archwire at mesial and distal ends of the orthodontic bracket. Orthodontists have sought the ability to increase the options available in ligating an archwire to a bracket.

Another important consideration in the design of a bracket is the structural integrity of the bracket. Due to its small size and the concentration of forces relative to the archwire slot, it is critical that the bracket is designed to withstand forces applied to it without failure.

It would be desirable to have a bracket design which reduces friction between the archwire and the archwire slot. It would be desirable to have a bracket design which permits easy, quick and accurate alignment with the crown long axis and with the occlusal plane. It would be desirable to have a bracket which is easy to identify. It would be desirable to have a bracket design which supports multiple ligation options. It would be desirable to have a bracket which is both small in size and structurally sound. It would be extremely advantageous to have a bracket design which incorporates all of the above features of reduced friction, accurate alignment, ease of identification, multiple ligation options, small size and structural integrity.

SUMMARY OF THE INVENTION

In accordance with one embodiment of the present invention, an orthodontic twin bracket is provided which includes: an occlusal tie wing having a mesial wing tip and a distal wing tip; a gingival tie wing having a mesial wing tip and a distal wing tip; and an archwire slot having an archwire floor and having two archwire side walls. The archwire slot further includes: at least one protrusion extending buccally from the archwire floor; two protrusions extending occlusally from a gingival side wall and having a gingivally-extending depression located between the two protrusions; and two protrusions extending gingivally from an occlusal side wall and having an occlusally-extending depression located between the two protrusions. The bracket also includes a base portion having a backside for attachment to a tooth.

Preferably, the orthodontic bracket further includes a hook extending from one of the wing tips.

Preferably, the hook is integrally formed into the bracket.

Preferably, the hook is capable of bending in two without breaking.

Preferably, the orthodontic bracket further includes a vertical slot with an opening in the base portion.

Preferably, the vertical slot is about 0.02 inches by 0.02 inches in cross-section.

Preferably, the archwire floor includes at least two protrusions extending buccally from the archwire floor and having a labially-extending depression located between the two protrusions.

Preferably, the two most buccally-extending portions of the two protrusions in the archwire floor are substantially aligned with the two most occlusally-extending portions of the two protrusions in the gingival side wall and the two most gingivally-extending portions of the two protrusions in the occlusal side wall.

Preferably, the depression located between the two protrusions in the archwire floor is substantially aligned with the depression located between the two protrusions in the gingival side wall and the depression located between the two protrusions in the occlusal side wall.

Preferably, the orthodontic bracket also includes a labially-extending saddle located between the two wing tips of the occlusal tie wing and a labially-extending saddle located between the two wing tips of the gingival tie wing.

Preferably, the orthodontic bracket also includes indicia formed in at least one of the wing tips.

Preferably, the bracket is a twin bracket and the side wall and floor protrusions are rounded.

Preferably, the bracket provides for reduced friction between the archwire slot and the archwire for better sliding mechanics.

Preferably, the bracket provides for increased archwire efficiency.

Preferably, during a phase of the orthodontic treatment in which out-of-alignment teeth are moved back into alignment, the orthodontic bracket provides improved continuous leveling force.

Preferably, the orthodontic bracket provides reduced binding between the archwire and bracket.

In one embodiment, the orthodontic twin bracket includes: (a) an occlusal tie wing having a mesial wing tip and a distal wing tip and a labially-extending saddle located between the mesial wing tip and the distal wing tip; (b) a gingival tie wing having a mesial wing tip and a distal wing tip and a labially-extending saddle located between the mesial wing tip and the distal wing tip; (c) an archwire slot having an archwire floor and having two archwire side walls, and further including: (i) at least one protrusion extending buccally from the archwire floor; (ii) two protrusions extending occlusally from a gingival side wall and having a gingivally-extending depression located between the two protrusions; and (iii) two protrusions extending gingivally from an occlusal side wall and having an occlusally-extending depression located between the two protrusions; the depression located between the two protrusions in the gingival side wall is substantially aligned with the depression located between the two protrusions in the occlusal side wall and the two most occlusally-extending portions of the two protrusions in the gingival side wall are substantially aligned with the two most gingivally-extending portions of the two protrusions in said occlusal side wall; (d) a base portion having a backside for attachment to a tooth; (e) a hook extending from one of the wing tips; (f) a vertical slot formed in the base portion; and (g) indicia formed in or on at least one of the wing tips.

In another embodiment, the orthodontic twin bracket includes: (a) an occlusal tie wing having a mesial wing tip and a distal wing tip and a labially-extending saddle located between the mesial wing tip and the distal wing tip; (b) a gingival tie wing having a mesial wing tip and a distal wing tip and a labially-extending saddle located between the mesial wing tip and said distal wing tip; (c) an archwire slot having an archwire floor and having two archwire side walls, and further including: (i) at least one protrusion extending buccally from the archwire floor; (ii) two protrusions extending occlusally from a gingival side wall and having a gingivally-extending depression located between the two protrusions; and (iii) two protrusions extending gingivally from an occlusal side wall and having an occlusally-extending depression located between the two protrusions; depression located between the two protrusions in the gingival side wall is substantially aligned with the depression located between the two protrusions in the occlusal side wall and the two most occlusally-extending portions of the two protrusions in the gingival side wall are substantially aligned with the two most gingivally-extending portions of the two protrusions in the occlusal side wall; (d) a base portion having a backside for attachment to a tooth; (e) a hook extending from one of the wing tips; (f) a vertical slot formed in the base portion; and (g) indicia formed in or on at least one of the wing tips; wherein the side wall and floor protrusions are rounded, the bracket provides for reduced friction between the archwire slot and the archwire for better sliding mechanics and increased archwire efficiency, during a phase of the orthodontic treatment in which out-of-alignment teeth are moved back into alignment, the orthodontic twin bracket provides improved continuous leveling force, and the bracket provides reduced binding between the archwire and the bracket.

In accordance with the present invention a bracket design is provided which reduces friction between the archwire and the archwire slot. In accordance with the present invention a bracket design is provided which permits easy, quick and accurate alignment with the crown long axis and with the occlusal plane. In accordance with the present invention a bracket is provided which is easy to identify. In accordance with the present invention a bracket design is provided which supports multiple ligation options. In accordance with the present invention a bracket is provided which is both small in size and structurally sound. In a preferred embodiment of the present invention, a bracket design is provided which incorporates all of the above features of reduced friction, accurate alignment, ease of identification, multiple ligation options, small size and structural integrity.

DETAILED DESCRIPTION OF THE INVENTION

Figure 1:
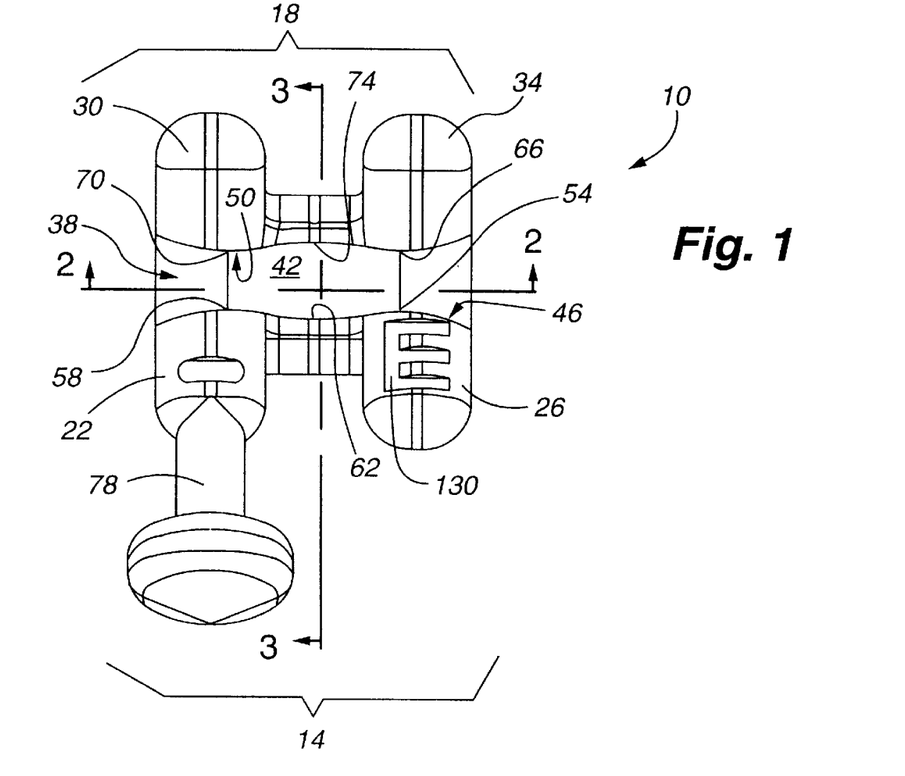
FIG. 1 illustrates a view of the buccal side of an orthodontic twin bracket in accordance with the present invention.

The present invention will be described in accordance with the accompanying Figures. FIG. 1 illustrates a view of the buccal side of the orthodontic twin bracket 10 in accordance with the present invention. The bracket 10 includes a gingival tie wing 14 and an occlusal tie wing 18. The gingival tie wing 14 includes a mesial wing tip 22 and a distal wing tip 26. The occlusal tie wing 18 includes a mesial wing tip 30 and a distal wing tip 34. Located between the gingival tie wing 14 and the occlusal tie wing 18 is a mesiodistal-extending archwire slot 38. The archwire slot 38 includes an archwire slot floor 42, a gingival side wall 46 and an occlusal side wall 50. The gingival side wall 46 includes two occlusally-extending protrusions, with the most occlusally-extending portions located at 54 and 58. Located between the two occlusally-extending protrusions is a gingivally-extending depression 62. The occlusal side wall 50 includes two gingivally-extending protrusions, with the most gingivally extending portions located at lines 66 and 70. Located between the two gingivally-extending protrusions is an occlusally-extending depression 74.

Preferably, the protrusions of the archwire side walls are rounded. Rounded archwire side walls can increase archwire effectiveness. Because the archwire is not rigidly captured, as is the case with conventional edgewise brackets, a gentler and more continuous treatment force is generated. Leveling at the beginning of treatment can be accomplished faster. Torque, tip and rotational forces can all be delivered more gently due to the fact that the archwire touches the bracket at the apex of the rounded side walls only. The line contact between the bracket and archwire effectively increases inter-bracket distance for a more active, nonbinding force.

The rounded archwire side wall feature makes archwire insertion easier and reduces discomfort between appointments. Advantages include one or more of the following: reduced friction for better sliding mechanics; increased archwire efficiency and continuity; gentler, more continuous leveling force; nonbinding; more gradual torque, tip and rotational force dissipation; and increased patient comfort.

Extending from wing tip 22 is an attachment knob or hook 78. Typically, the hook 78 is on the gingival side of the bracket 10. The hook 78 can be used in conjunction with springs, ligation doughnuts, elastic ribbons, etc. to perform various tasks such as pulling another tooth into place, connecting the maxillary with the mandibular using elastics, etc. Preferably the hook 78 is located on the gingival side of a brackets designed for cuspids and bicuspids (e.g., see FIGS. 1, 9, 10, 12, 13 and 14).

Figure 2:
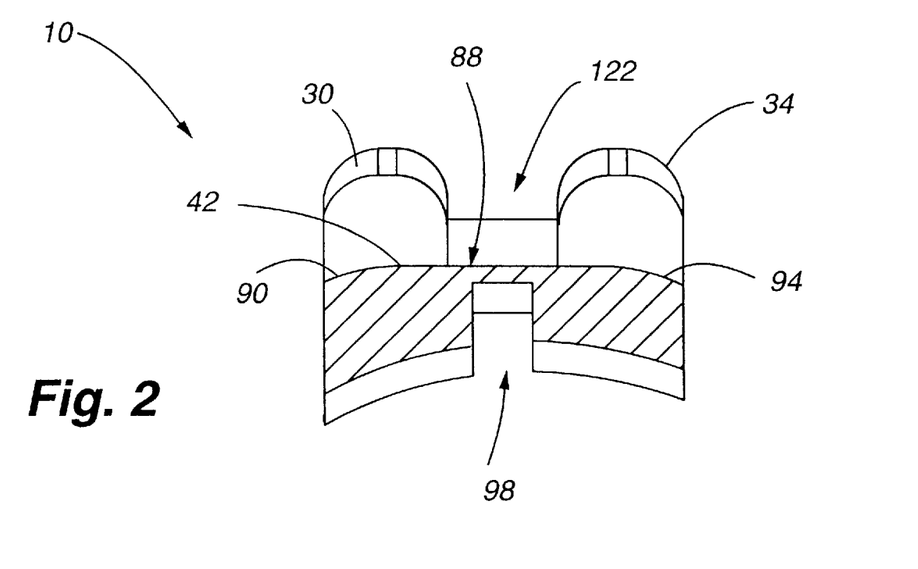
FIG. 2 illustrates a cutaway view of another embodiment of an orthodontic bracket of the type shown in FIG. 1 taken along lines 2—2 of FIG. 1.
Figure 2A:
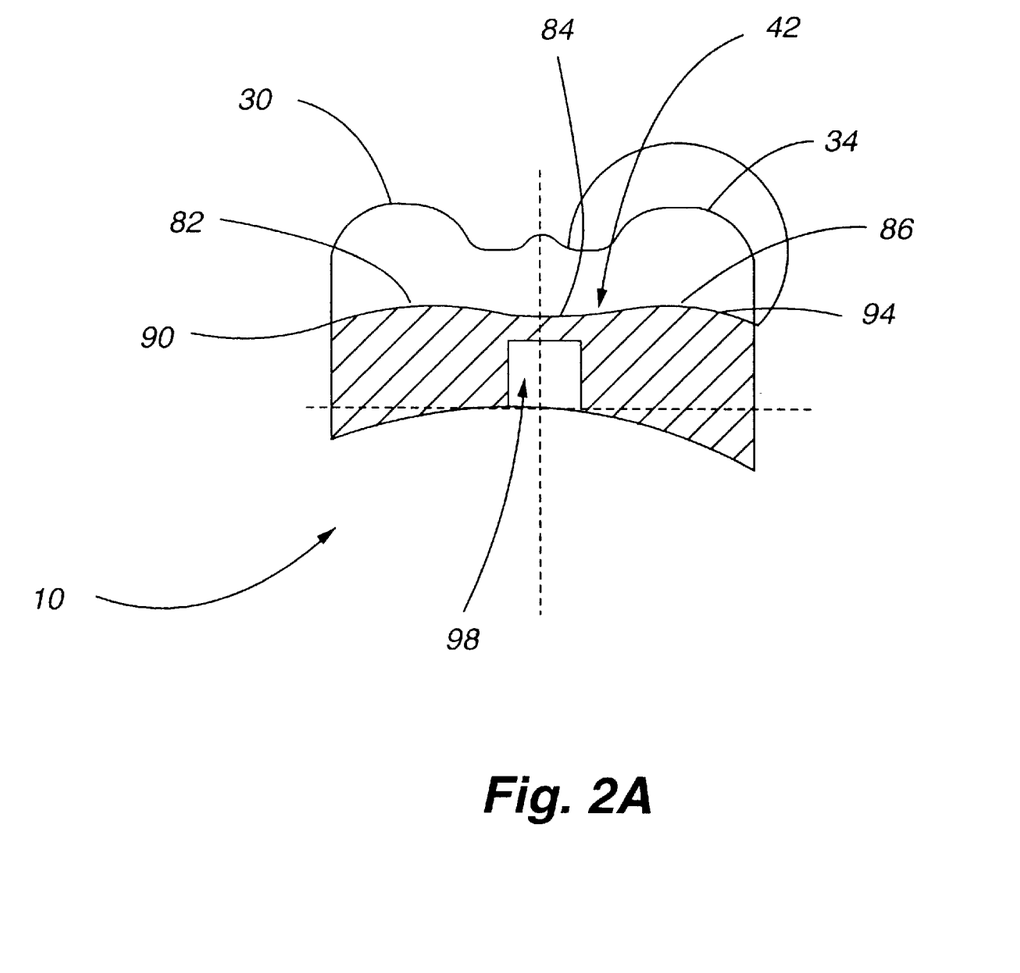
FIG. 2A illustrates a cutaway view of one embodiment of an orthodontic bracket in accordance with the present invention.

In one embodiment of the present invention, two protrusions 82,86 extend buccally from the archwire floor 42 of the bracket 10 and are best illustrated in FIG. 2A. The most buccally-extending portions of the archwire floor 42 are substantially at lines 82 and 86. Located between the two buccally-extending protrusions 82, 86 is a labially-extending depression 84. The shape of the archwire floor 42 provides a number of advantages. For example, the mesial and distal ends 90,94 of the archwire floor 42 slope in a labial direction. This reduces friction by reducing the area of the contact between the archwire floor 42 and the archwire (not shown). This also provides greater freedom of the entrance angle for the archwire. In this way, an orthodontist is given greater flexibility to provide appropriate corrective forces to a patient's teeth. Because the entrance to the archwire slot 42 is larger than the archwire, easier threading of the archwire through the brackets 10 is provided, in much the same manner that a countersink simplifies the placement of a screw in a pre-drilled hole. The labially-extending depression 84 also helps to reduce friction between the archwire floor 42 and the archwire, by reducing contact between the two. In an alternative embodiment, shown in FIG. 2, there is a single wider protrusion 88. The mesial and distal ends 90,94 of the archwire floor 42 still slope in a labial direction, similar to the embodiment shown in FIG. 2, but there is no central labially-extending depression 84.

The rounded archwire floor 42 provides improved control, and in particular, improved rotational control. In the embodiment having a labially-extending depression 84 (e.g., see FIG. 2A), the rounded archwire floor contacts the archwire substantially at only two lines, thus reducing archwire/bracket friction. Even the binding of woven or braided archwires is reduced because the sharp ends of the conventional flat bracket floors are gone. Advantages can include: less archwire/bracket friction which can result in more effective movement; less binding, notching or kinking of archwires; better mechanics, regardless of initial archwire curvature or entry/exit vector; normal rotational control; and increased effective inter-bracket distance.

Also illustrated in FIG. 2 is a centrally located auxiliary (or vertical) slot 98. When the bracket 10 is mounted on a patient's tooth in the normal orientation, the auxiliary slot 98 will be oriented in a substantially vertical orientation. The auxiliary slot 98 allows the practitioner options and flexibility by permitting the use of auxiliary devices, such as power pins, rotating springs and uprighting springs. The auxiliary slot 98, when used in conjunction with such auxiliary devices, provides the orthodontist greater treatment flexibility, for example in tipping a tooth. In one embodiment, the auxiliary slot is 0.020×0.020 inches in cross section. Surprisingly, it has been found that in certain embodiments of the present invention, the auxiliary slot 98 can be located under the central portion of the archwire slot floor 42 without unduly affecting the structural integrity of the bracket 10. An important consideration in determining whether a bracket can include both a central labially-extending depression 84 and a centrally-located auxiliary slot 98 is the in/out of the bracket. As used herein, the term "in/out" is defined to mean the distance from the bottom of the archwire slot to the tooth surface. The in/out can vary depending on the desired result of the corrective orthodontic treatment. When the in/out is shallow, the central labially-extending depression 84 can be designed to be shallower or eliminated altogether. This is a design trade-off between reduced friction vs. structural integrity. Preferably, a low bracket profile is maintained, even with the vertical slot 98.

Figure 3:
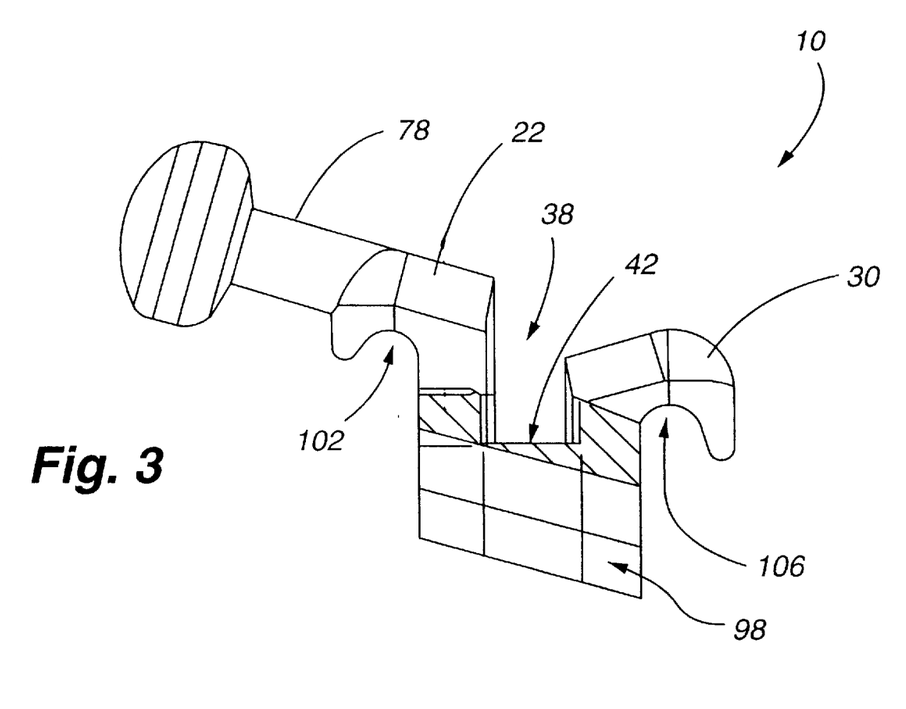
FIG. 3 illustrates a cutaway view of the orthodontic bracket of FIG. 1 taken along lines 3—3 of FIG. 1.

FIG. 3 illustrates a side cutaway view of the bracket 10 taken along lines 3—3 of FIG. 1. FIG. 3 illustrates the mesial wing 22 of the gingival tie wing 14 and the mesial wing tip 30 of the occlusal tie wing 18. A side view of the auxiliary slot 98 and an end view of the archwire slot 38 are shown in FIG. 3. Ligature undercuts 102,106 are also clearly illustrated in FIG. 3.

Figure 4:
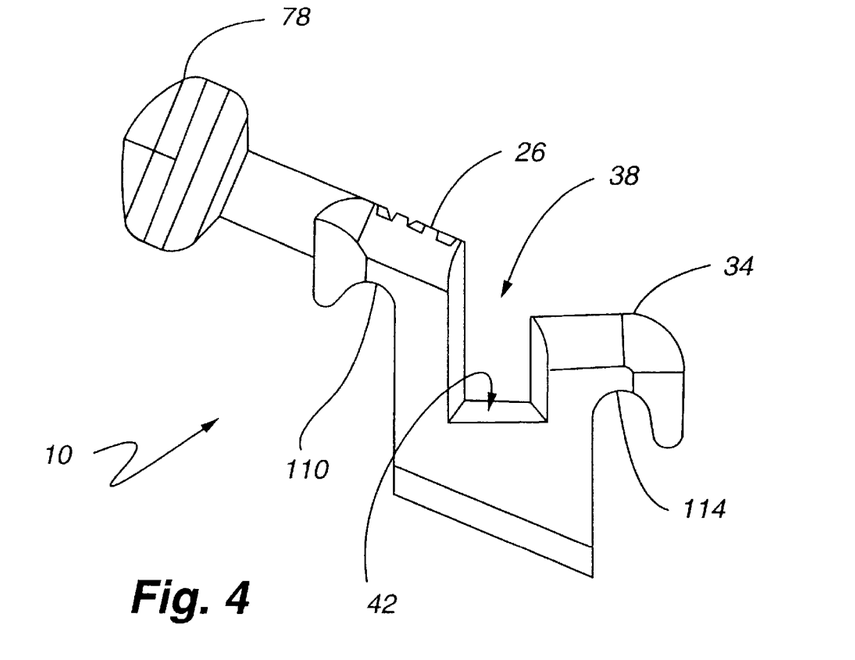
FIG. 4 illustrates an end view of the orthodontic bracket of FIG. 1.

FIG. 4 is a view of the bracket 10 from the same end as FIG. 3, however, it is not a cutaway view. Distal wing tips 26,34 with the corresponding distal ligature undercuts 110, 114 are clearly illustrated in FIG. 4.

Figure 5:
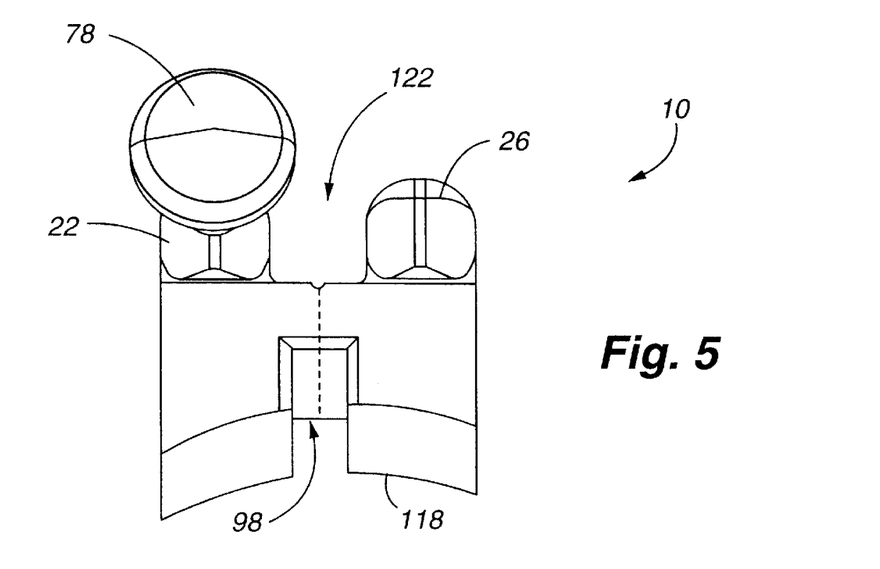
FIG. 5 illustrates the gingival side of the orthodontic bracket of FIG. 1.
Figure 7:
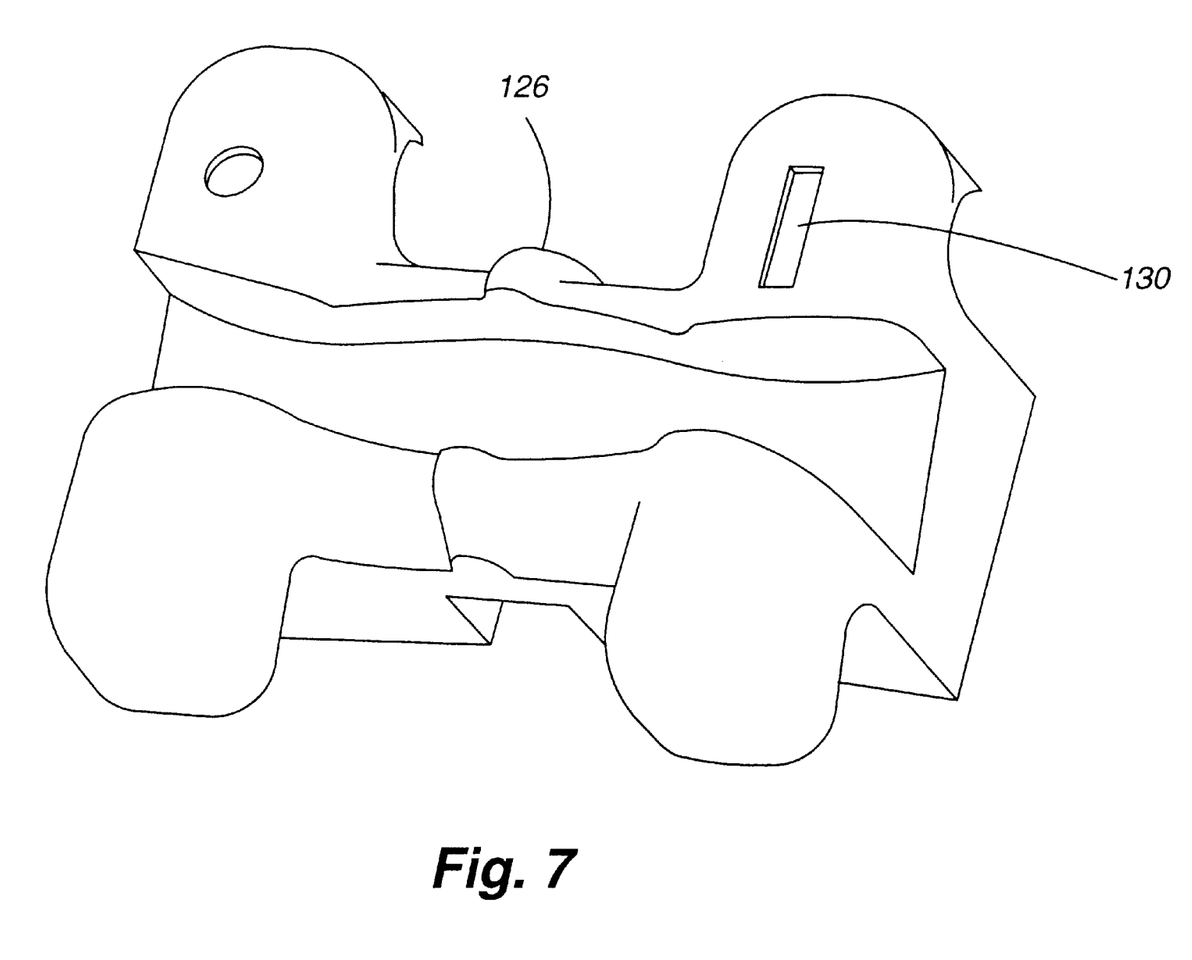
FIG. 7 illustrates a perspective view of an orthodontic bracket designed to go on the maxillary central teeth.

FIG. 5 shows bracket 10 from the gingival side. The base portion 118 of the bracket 10 and the open area or saddle 122 between the mesial wing tips 22,30 and the distal wing tips 26,34 are clearly illustrated. The saddle 122 permits the use of ligatures to hold down the archwire to be applied in various configurations. For example, the ligature can pass under the two mesial wing tips 22, 30, under the two distal wing tips 26,34, or under all four wing tips 22,26,30,34. This allows the orthodontist to induce rotation by placing more pressure on one end of the bracket or another, or applying pressure evenly. Preferably, the saddle 122 includes a central saddle ridge 126 (FIG. 7). The saddle ridge 126 can provide a number of advantages. For example, it maintains the ligature in a desired location, it can help support the ligature above the top surface of the archwire, thus reducing friction, and it can improve the structural integrity of the bracket 10.

Another advantage of the saddle 122 and the saddle ridge 126 is that they are perpendicular to the base radius, thereby providing a convenient sight line, or centering mark, to assist in the placement of the bracket 10 relative to the long axis of the tooth. In embodiments of the bracket 10 which have a vertical slot 98, the vertical slot 98 can also be employed to assist in the proper positioning of the bracket 10 relative to the long axis of the tooth.

Figure 6:
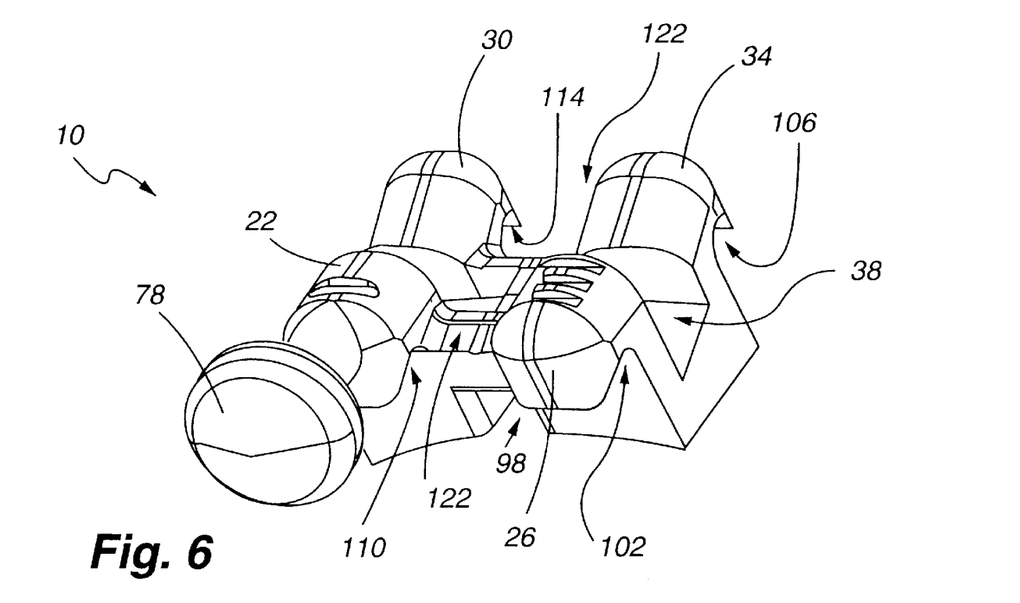
FIG. 6 illustrates a perspective view of the orthodontic bracket of FIG. 1.

FIG. 6 is a perspective view of bracket 10, providing a good illustration of the interaction between the archwire slot 38, the ligature undercuts 102,106,110,114 and the saddle 122. FIG. 7 illustrates a perspective view of an orthodontic bracket designed to go on the maxillary central teeth. The saddle ridge 126 is clearly illustrated in FIGS. 7–14. FIGS. 6–14 clearly illustrate how all surfaces and outer edges are preferably rounded and contoured for supreme patient comfort.

Figure 8:
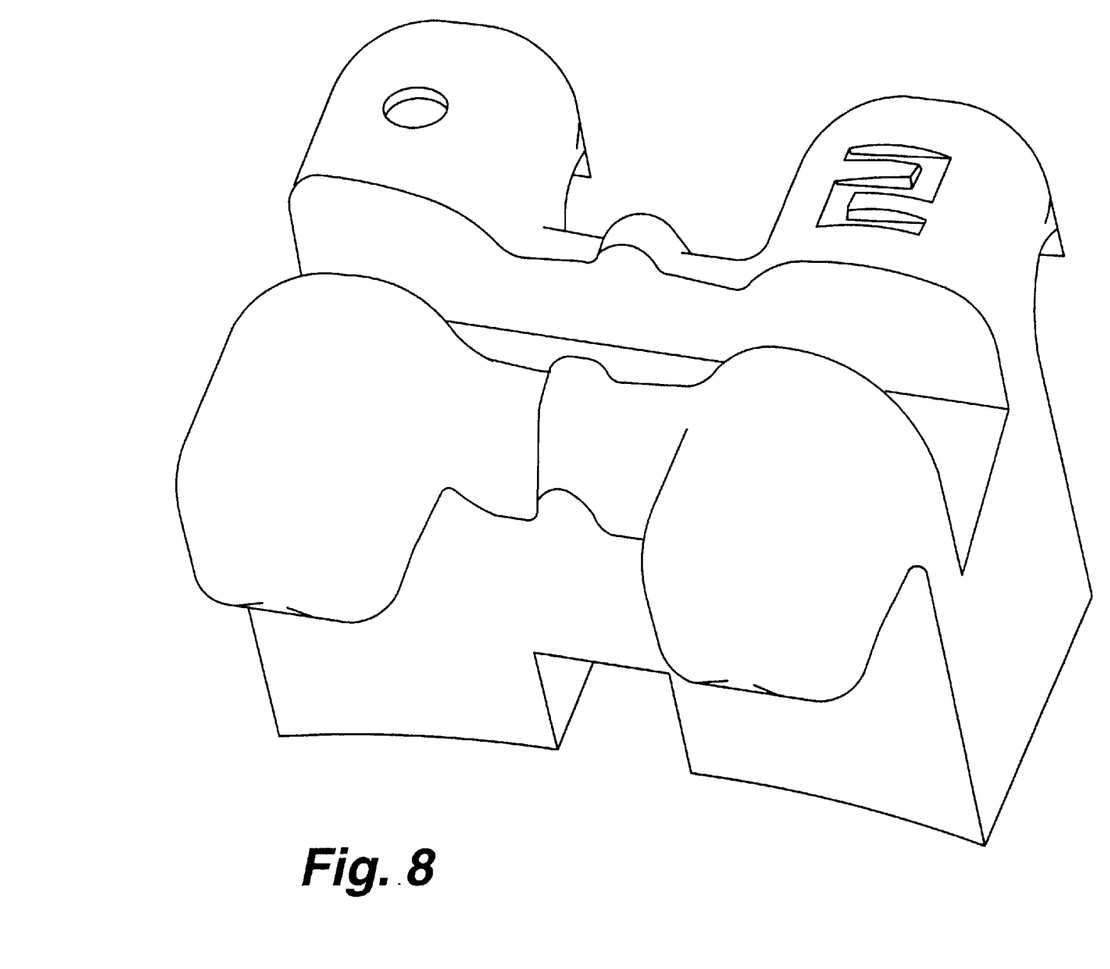
FIG. 8 illustrates a perspective view of an orthodontic bracket designed to go on the maxillary lateral teeth.
Figure 9:
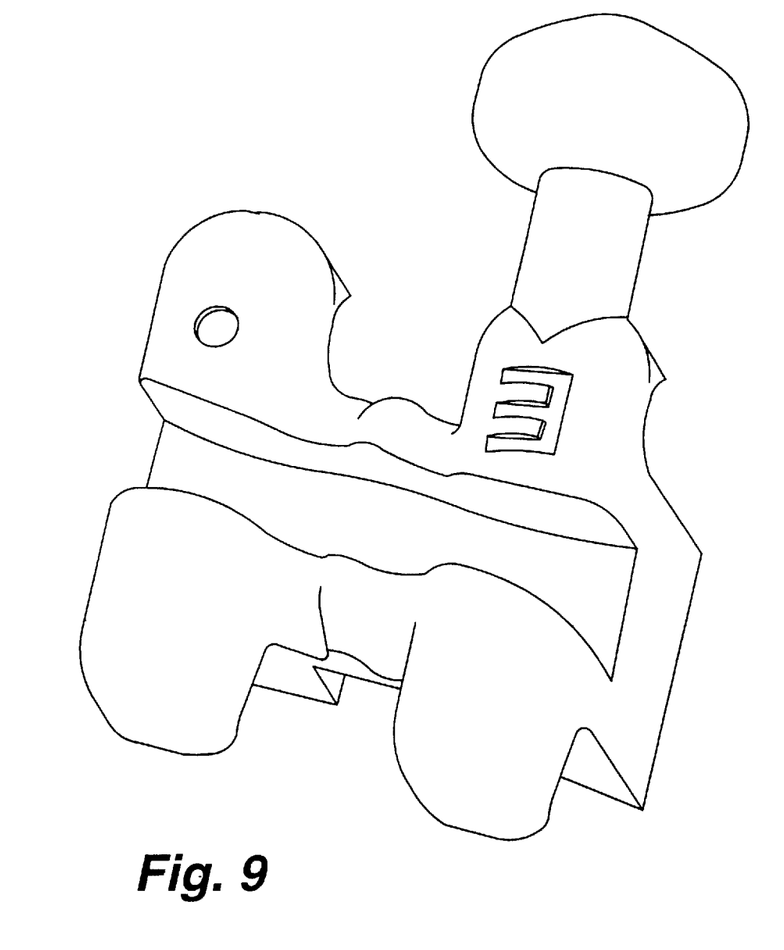
FIG. 9 illustrates a perspective view of an orthodontic bracket designed to go on the maxillary cuspid teeth.
Figure 10:
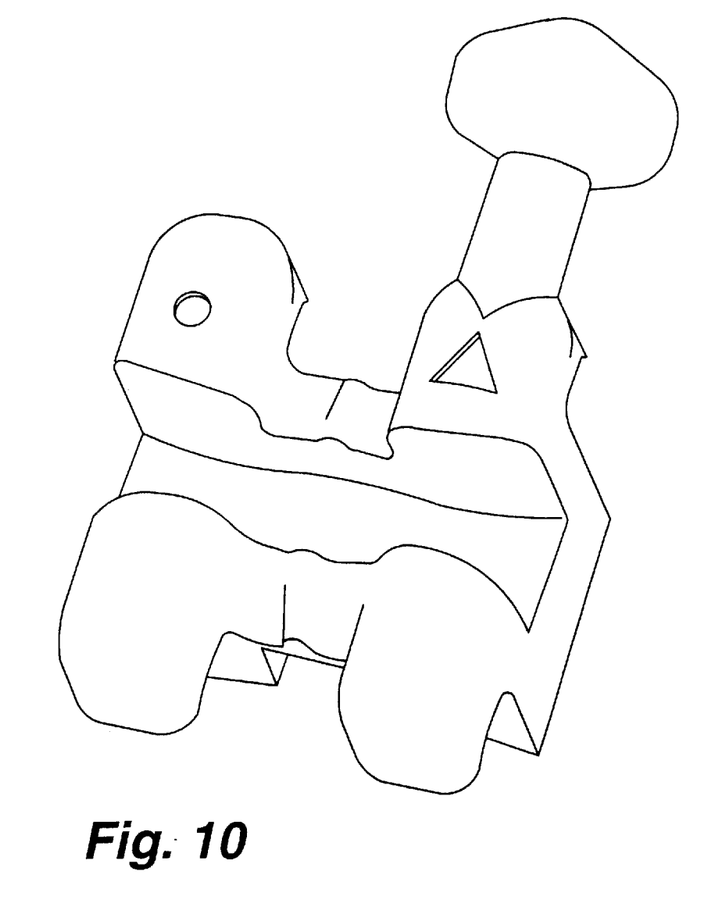
FIG. 10 illustrates a perspective view of an orthodontic bracket designed to go on the maxillary first and second bicuspid teeth.
Figure 11:
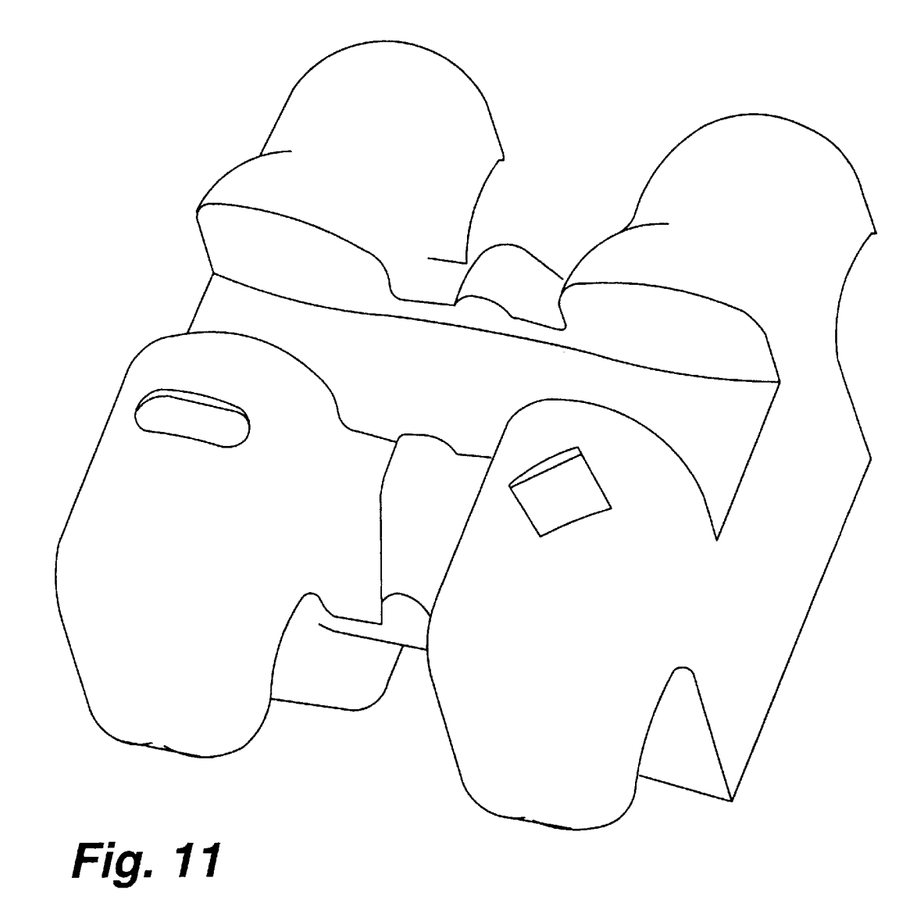
FIG. 11 illustrates a perspective view of an orthodontic bracket designed to go on the mandibular central and lateral teeth.
Figure 12:
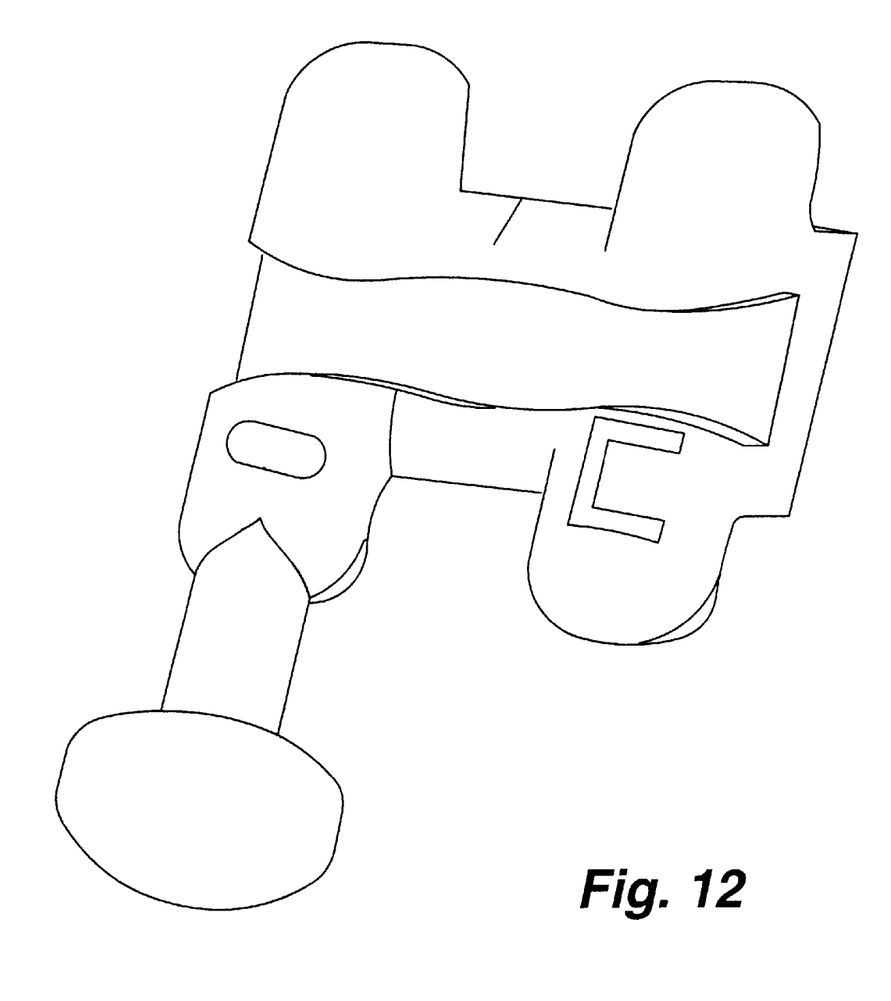
FIG. 12 illustrates a perspective view of an orthodontic bracket designed to go on the mandibular cuspid teeth.
Figure 13:
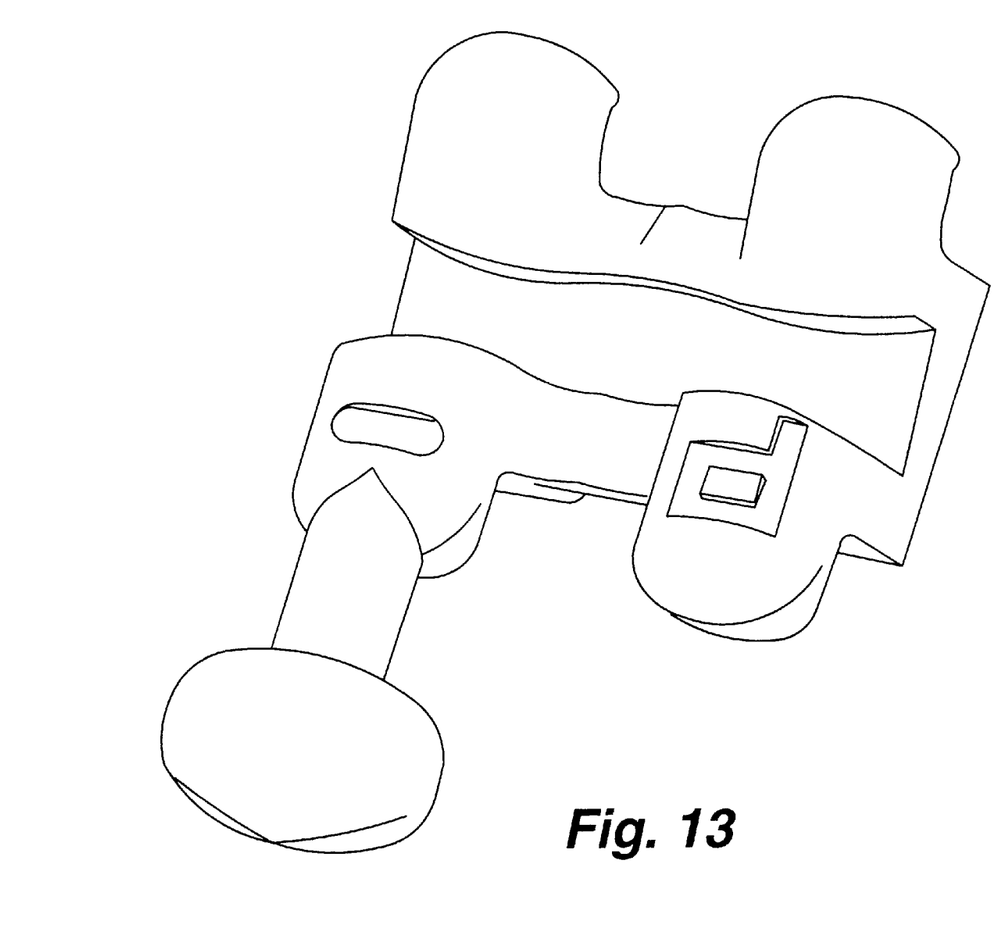
FIG. 13 illustrates a perspective view of an orthodontic bracket designed to go on the mandibular first bicuspid teeth.
Figure 14:
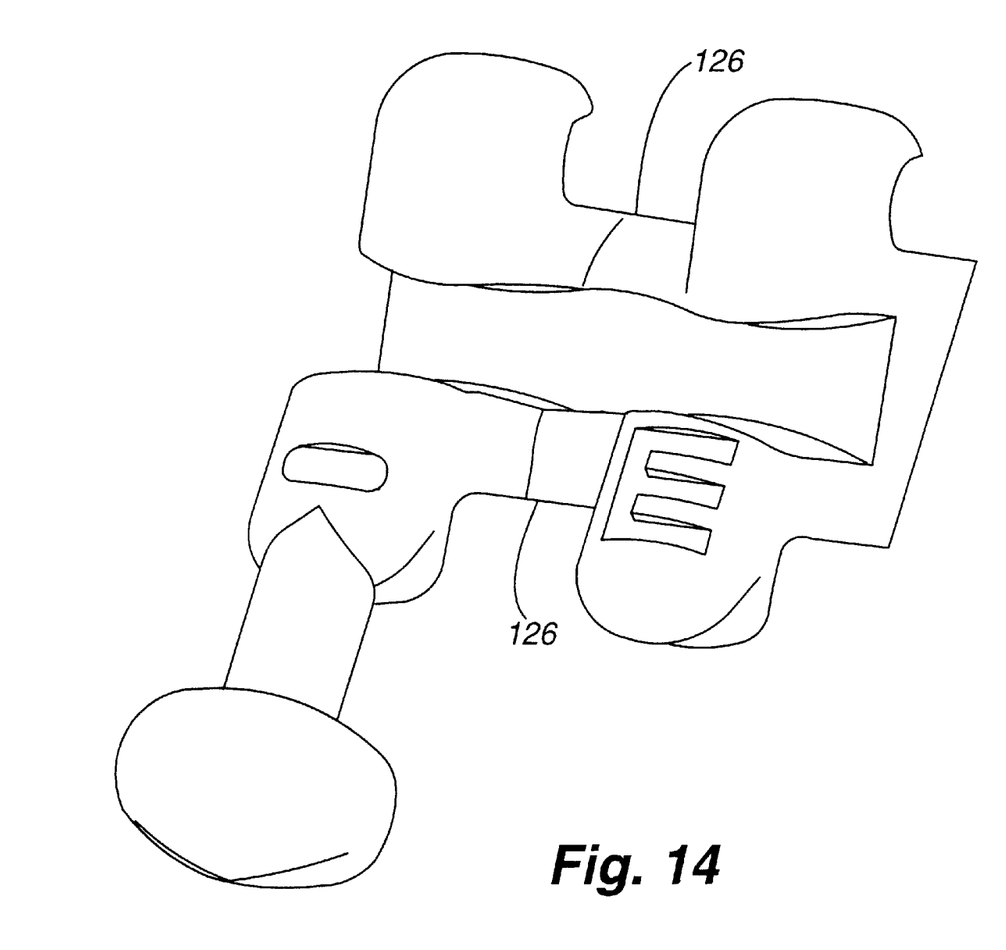
FIG. 14 illustrates a perspective view of an orthodontic bracket designed to go on the mandibular second bicuspid teeth.

FIG. 8 illustrates a perspective view of an orthodontic bracket designed to go on the maxillary lateral teeth. FIG. 9 illustrates a perspective view of an orthodontic bracket designed to go on the maxillary cuspid teeth. FIG. 10 illustrates a perspective view of an orthodontic bracket designed to go on the maxillary first and second bicuspid teeth. FIG. 11 illustrates a perspective view of an orthodontic bracket designed to go on the mandibular central and lateral teeth. FIG. 12 illustrates a perspective view of an orthodontic bracket designed to go on the mandibular cuspid teeth. FIG. 13 illustrates a perspective view of an orthodontic bracket designed to go on the mandibular first bicuspid teeth. FIG. 14 illustrates a perspective view of an orthodontic bracket designed to go on the mandibular second bicuspid teeth. FIG. 14 illustrates a modified version of the bracket illustrated in FIGS. 1–6. The bracket of FIG. 14 has a saddle ridge 126.

The brackets can have various dimensions. Preferably, the brackets are narrow, because it is desirable to have the maximum spacing between the brackets. For example the bracket designed for the maxillary central teeth shown in FIG. 7 is preferably about 0.14 inches wide. The bracket designed for the maxillary lateral teeth shown in FIG. 8 is preferably about 0.092 inches wide. Preferably the rest of the brackets illustrated in FIGS. 9–14 are about 0.116 inches wide.

As illustrated in FIGS. 1–14, indicia 130 can be formed into at least one wing tip. In one embodiment, the maxillary brackets have indicia which include numerals, such as the 1, 2, 3 shown in FIGS. 7, 8, 9, respectively. In one embodiment, the brackets which can be used on maxillary or mandibular teeth have geometric indicia, such as the triangle in FIG. 10 or the diamond in FIG. 11. The brackets designed for the mandibular teeth shown in FIGS. 12–14 include letters as part of the indicia, for example, c, d, and e. The indicia can be permanent or ink markings, or a combination of permanent and ink markings.

Bracket and tube bonding bases can be customized for left/right tooth anatomy and to smoothly follow the facial and labial/buccal surface of the tooth. Foil mesh bases can be delicately balanced with the smallest possible bases and a surface area large enough for solid adhesion.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An orthodontic bracket comprising:
   (a) an occlusal tie wing having a mesial wing tip and a distal wing tip;
   (b) a gingival tie wing having a mesial wing tip and a distal wing tip;
   (c) an archwire slot having an archwire floor and having two archwire side walls, and further comprising:
      (i) at least one protrusion extending buccally from said archwire floor;
      (ii) two protrusions extending occlusally from a gingival side wall and having a gingivally-extending depression located between said two protrusions; and
      (iii) two protrusions extending gingivally from an occlusal side wall and having an occlusally-extending depression located between said two protrusions;
   (d) a base portion having a backside for attachment to a tooth; and
   (e) a saddle ridge located between said mesial wing tip and said distal wing tip of at least one of said occlusal or said gingival tie wings, wherein said saddle ridge is recessed relative to at least one of said mesial wing tip or said distal wing tip, of at least one of said occlusal tie wing or said gingival tie wing.

2. The orthodontic bracket of claim 1, wherein said saddle ridge has a rounded buccal face.

3. The orthodontic bracket of claim 1, wherein said saddle ridge is mesial-distally centered between said mesial wing tip and said distal wing tip, of at least one of said occlusal or said gingival tie wings.

4. The orthodontic bracket of claim 1, wherein said saddle ridge improves the structural integrity of said bracket.

5. The orthodontic bracket of claim 1, wherein said saddle ridge creates a convex structure between said mesial wing tip and said distal wing tip of either of said occlusal tie wing or said gingival tie wing.

6. An orthodontic bracket comprising:
   (a) an occlusal tie wing having a mesial wing tip and a distal wing tip;
   (b) a gingival tie wing having a mesial wing tip and a distal wing tip;
   (c) an archwire slot having an archwire floor and having two archwire side walls, and further comprising:
      (i) at least one protrusion extending buccally from said archwire floor;
      (ii) two protrusions extending occlusally from a gingival side wall and having a gingivally-extending depression located between said two protrusions; and
      (iii) two protrusions extending gingivally from an occlusal side wall and having an occlusally-extending depression located between said two protrusions;
   (d) a base portion having a backside for attachment to a tooth; and
   (e) a saddle ridge located between said mesial wing tip and said distal wing tip of at least one of said occlusal or said gingival tie wings, wherein said saddle ridge includes a rounded buccal face situated lingually to the buccal face portions of said mesial wing tip and said distal wing tip, of at least one of said occlusal tie wing or said gingival tie wing.

7. The orthodontic bracket of claim 6, wherein said saddle ridge is mesial-distally centered between said mesial wing tip and said distal wing tip, of at least one of said occlusal or said gingival tie wings.

8. The orthodontic bracket of claim 6, wherein said saddle ridge improves the structural integrity of said bracket.

9. The orthodontic bracket of claim 6, wherein said saddle ridge creates a convex structure between said mesial wing tip and said distal wing tip of either of said occlusal tie wing or said gingival tie wing.

* * * * *